United States Patent [19]
Lentz et al.

[11] Patent Number: 5,583,102
[45] Date of Patent: Dec. 10, 1996

[54] HUMAN THROMBOMODULIN IN WOUND HEALING

[75] Inventors: Steven R. Lentz; Thomas J. Raife; Donna J. Lager, all of Iowa City, Iowa

[73] Assignee: University of Iowa Research Foundation, Oakdale, Iowa

[21] Appl. No.: 162,462

[22] Filed: Dec. 3, 1993

[51] Int. Cl.$^6$ .......................... A61K 38/16; A61K 38/17; C07K 14/435; C07K 14/47
[52] U.S. Cl. .................. 514/8; 514/12; 514/21; 530/350
[58] Field of Search .................. 514/8, 12, 21; 530/350

[56] References Cited

U.S. PATENT DOCUMENTS

| | | | |
|---|---|---|---|
| 4,912,207 | 3/1990 | Majerus et al. | 536/27 |
| 5,126,140 | 6/1992 | Ito et al. | 424/423 |

OTHER PUBLICATIONS

Lentz, Sequences Required for Thrombomodulin Cofactor Activity Within the Fourth Epidermal Growth Factor–Like Domain of Human Thrombomodulin, 1993 Journal of Biological Chemistry, 268:15312–15317.

Carney, The Role of Thrombin and Thrombin Receptor Activating Peptide (Trap–508) in Initiation of Tissue Repair, Thrombosis and Haemostasis 158–162.

Clark, Cutaneous Wound Repair, "Physiology, Biochemistry, and Molecular Biology of the Skin", L. A. Goldsmith, editor, Oxford Press, New York 1991.

McCachren et al. "Thrombomodulin Expression By Human Blood Monocytes and by Human Synovial Tissue Lining Macrophages" Blood 78(12) 3128–3132 1991.

*Primary Examiner*—Mindy Fleisher
*Assistant Examiner*—Nancy J. Degen
*Attorney, Agent, or Firm*—Zarley, McKee, Thomte, Voorhees, & Sease

[57] ABSTRACT

The use of human thrombomodulin and acceptable derivatives thereof as an agent for stimulating wound regeneration including epithilial cell differentiation is disclosed.

18 Claims, 5 Drawing Sheets
(6 of 9 Drawing(s) in Color)

HUMAN THROMBOMODULIN IN WOUND HEALING

GRANT REFERENCE

This invention was made with government support under Contract No. AR-41728 and T32-HL-07344 awarded by the National Institutes of Health. The government has certain rights in the invention.

BACKGROUND OF THE INVENTION

Coagulation or clotting of blood involves a highly complex process of a series of interactions between several enzymes and substrates. At its simplest level it involves thromboplastin (or tissue factor), an enzyme produced by damaged tissue which converts a protein in the plasma, prothrombin, into thrombin. Thrombin then converts another plasma protein, fibrinogen, into fibrin, a filamentous protein which forms a mesh work in which red and white blood cells and platlets become entangled.

This classic model provides an oversimplified version of the clotting process as numerous other enzymes are involved. For example Factor III, tissue factor; Factor IV, calcium ions; Factor V, an unstable protein substance proaccelerin; Factor VII, proconvertin or serum prothrombin conversion accelerator; Factor VIII antihemophilic factor; Factor IX Christmas factor; Factor X Stuart-Prower factor; Factor XI plasma thromboplastin anticedent (PTA); Factor XII Hageman or glass factor; Factor XIII fibrin stabilizing factor (FSF); and prekallikrein, also called Fletcher Factor just to name a few. This initial provisional matrix of fibrin and fibronectin produced through activation of these hemostatic pathways constitutes the first phase (Inflammatory Phase) of a cutaneous wound repair. Traditionally neutrophils infiltrate the provisional matrix followed by monocytes and macrophages.

The next stage includes new tissue reformation. During this stage re-epithelialization is produced by migration and proliferation of basal keratinocytes over the provisional matrix. Granulation tissue is formed through macrophage accumulation, fibroblast ingrowth, and angiogenosis. Proliferation of myofibroblasts leads to contraction of the wound.

The final phase includes matrix remodeling in which down-regulation of fibroblast proliferation is necessary for wound maturation and prevention of hypertrophic scar formation. During this phase, fibronectin is removed from the matrix and replaced by proteoglycans and fibrous bundles of type I collagen.

Several physiological mediators have been proposed to stimulate various aspects of the three phases of cutaneous wound repair. Among the proposed mediators are fibrin, components of the complement pathway, platelet-derived growth factor (PDGF), keratinocyte growth factor (KGF), transforming growth factors $\alpha$ and $\beta$, fibroblast growth factors, and epidermal growth factor (EGF).

More recently, thrombin has become recognized as a potential stimulator of keratinocytes, fibroblasts, macrophages, and endothelial cells during wound healing. These effects of thrombin appear to be mediated partly through stimulation of a proteolytically-activated thrombin receptor, and partly through other unidentified receptors. Thrombomodulin inhibits thrombin-mediated stimulation through multiple mechanisms. First, thrombomodulin directly inhibits stimulation through the proteolytically-activated receptor by competing for thrombin binding. Second, thrombomodulin stimulates the protein C anticoagulant pathway, which decreases thrombin production, thereby indirectly inhibiting thrombin stimulation through all receptors.

More specifically thrombomodulin forms an approximately one-to-one stoichiometric complex with thrombin. In this complex form, thrombin fails to react with its natural substrates including fibrinogen, Factor V and platelets. Additionally this complex when formed, enhances the ability of thrombin to activate protein C more than 1,000 fold. Activated protein C functions as a potent natural anticoagulant by inactivating coagulation factors Va and VIIIa. Thus thrombomodulin functions to convert thrombin from a procoagulant protease to an anticoagulant.

Thrombomodulin was initially identified as an endothelial cell protein and immunohistochemical studies have demonstrated it to be present on endothelial cells throughout the vasculature. Constitutive expression of thrombomodulin on the luminal surface of blood vessels localizes coagulation to sites of vascular injury.

Thrombomodulin has been proposed to be a specific marker for cells of endothelial origin. However thrombomodulin is also synthesized in varying amounts by other types of cells including syncytiotrophoblast platelets megakaryocytes, monocytes, neutrophils, and synovial lining cells.

The association of cutaneous thrombosis with severe protein C deficiency suggests that the thrombomodulin/ protein C pathway is particularly important in skin. Thrombomodulin is known to be expressed by endothelial cells of dermal vessels. Attempts to identify thrombomodulin as present in human epidermis, a nonvascular tissue, however, have been inconclusive to date.

Thrombomodulin was initially identified and purified in 1981 as an endothelial cell co-factor for activation of the anticoagulant protein C. The cDNA for human thrombomodulin was subsequently cloned by three groups (in Saint Louis, Boston, and Japan) in 1987. Human thrombomodulin is currently being developed for therapeutic use as an anticoagulant.

This invention relates to the discovery that thrombomodulin regulates thrombin function not only during primary hemostasis but also during the processes of wound healing and tissue repair. Evidence exists that thrombin is involved in angiogenesis (by stimulating vascular endothelial cell proliferation), granulation tissue formation (by stimulating macrophages and fibroblasts), and re-epithelialization (by activating basal layer keratinocytes). Thus disordered wound healing (such as excessive scar formation or chronic ulceration) could be controlled by regulating thrombin activity by thrombomodulin. A similar process may occur in non-cutaneous wounds such as those in the gastrointestinal or urinary tracts.

It is an object of the present invention to provide a method of enhancing wound healing by regulating thrombin activity through introduction of thrombomodulin to sites of wound repair.

It is yet another object of the present invention to further study and disclose the role of thrombomodulin in wound healing and epithelial cell differentiation.

Yet another object is to provide agents to help prevent scar formation from cutaneous injuries.

Yet another object is to provide a method for preventing excess scarring by use of thrombomodulin.

SUMMARY OF THE INVENTION

The present invention relates to the discovery that thrombomodulin, previously thought to be involved primarily in blood clotting may also stimulate wound regeneration at sites of cutaneous injury. Investigation of the expression of thrombomodulin by human keratinocytes have indicated that thrombomodulin expression correlates strongly with keratinocyte differentiation, an essential feature of wound regeneration, thus establishing the ability of thrombomodulin to act as therapeutic agent for stimulation wound regeneration.

BRIEF DESCRIPTION OF DRAWINGS

The file of this patent contains at least one drawing executed in color. Copies of this patent with colored drawing(s) will be provided by the Patent and Trademark Office upon request and payment of the necessary fee.

DETAILED DESCRIPTION OF THE INVENTION

Figure 1A:
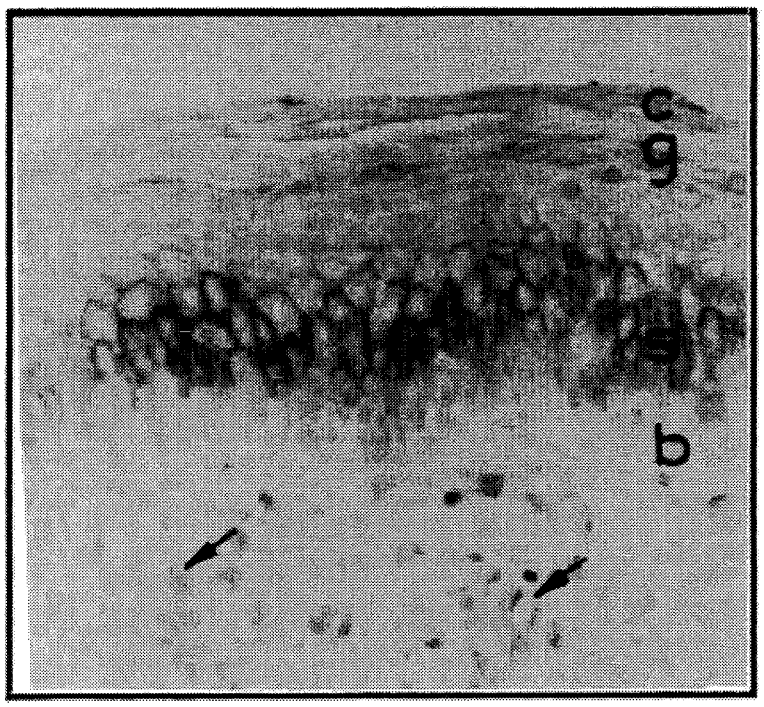
FIGS. 1A–1F indicate the immunohistochemical localization of thrombomodulin in normal epidermis and epidermal malignancies. (A) normal skin stained with mouse anti-thrombomodulin IgG (×250). Strong thrombomodulin staining is seen in the spinous layers of epidermis (s), and in dermal capillary endothelial cells (arrows). No staining is seen in the basal layer (b), weak staining is observed in the granular layer (g), and no staining is seen in the cornified layer (c). (B) No specific staining of normal skin is seen with pre-immune mouse serum (×250). (C) Invasive squamous cell carcinoma stained for thrombomodulin (×150). Within invasive foci, strong staining of peripheral cells and weak or absent staining of central, highly keratinized cells is seen (*). (D) Invasive squamous cell carcinoma stained with hematoxylin and eosin (×150), showing focus of highly keratinized cells (*). (E) Higher magnification view of invasive squamous cell carcinoma stained for thrombomodulin reveals peripheral staining of individual cells (×450). (F) Basal cell carcinoma stained for thrombomodulin showing no staining of neoplastic cells (×150). Thrombomodulin staining is present in the spinous layers of overlying normal epidermis, and in vascular endothelial cells (arrows).

According to the present invention it has been found that human thrombomodulin activity correlates with epidermal differentiation, and wound repair. Thus thrombomodulin acts not only as an anticoagulant but also, unexpectedly, it regulates epidermal differentiation. It was also found that thrombomodulin is synthesized by suprabasal spinous keratinocytes of the skin, and that this keratinocyte thrombomodulin is functional as an anticoagulant.

The stratified squamous epithelium of normal epidermis is composed of a single basal layer of mitotically active, relatively undifferentiated cells, and several suprabasal layers of terminally-differentiating, post-mytotic keratinocytes. It has been observed that thrombomodulin was selectively expressed in keratinocytes of the suprabasal spinous layer; no thrombomodulin was detected in the basal layer, and little thrombomodulin was seen in the superficial granular or cornified layers. Thus thrombomodulin expression is induced shortly after basal keratinocytes become committed to a program of terminal differentiation.

A correlation between thrombomodulin expression and epidermal differentiation was also observed in epidermal malignancies with little or no thrombomodulin staining detected in basal cell carcinomas and strong thrombomodulin staining observed in squamous cell carcinomas. The intensity of thrombomodulin staining was strongest in peripheral, non keratinized cells and weakest in central, highly keratinized cells. This pattern is similar to the strong staining of non keratinized spinous cells and weak staining of keratinized granular cells observed in normal epidermis.

Thrombomodulin staining was also detected in five cases of squamous cell carcinoma-in-situ. Thrombomodulin synthesis is a consistant feature of keratinocytes undergoing squamous differentiation. Measurement of functional activity of keratinocyte thrombomodulin through primary keratinocyte cultures indicated that proliferating keratinocytes produced functional thrombomodulin in amounts comparable to Human Umbilical Vein Endothelial Cells (HUVEC), and the cofactor activity of keratinocyte thrombomodulin increased significantly in response to an increase in extra cellular calcium ion concentration. Calcium stimulation reproduces several features of terminal keratinocyte differentiation and facilitates the ability of relatively undifferentiated keratinocytes to stratify and form cornified envelope proteins. Thrombomodulin cofactor activity, antigen and mRNA increased coordinately in keratinocytes incubated with 1.4 mM calcium chloride for 48 hours. Thus the activity of keratinocyte thrombomodulin is regulated primarily by the level of thrombomodulin mRNA.

This pattern of expression of thrombomodulin in epidermis indicates its function in wound healing. After cutaneous injury primary hemostasis is achieved by formation of a platelet/fibrin plug. Subsequently granulation tissue is produced and an expansion of basal layer of keratinocytes leads to re-epithelialization of the wound. Thrombin has been proposed to stimulate both granulation tissue formation and keratinocyte activation. Many thrombin-responsive cells express signal transducing thrombin receptors identical to the recently cloned platelet thrombin receptor. Thrombomodulin inhibits thrombin mediated signaling through this receptor by competing for thrombin binding. Therefore the production of thrombomodulin by differentiating keratinocytes inhibits thrombin stimulated cellular processes associated with tissue repair. Regulation of thrombin activity within the epidermis may also modulate the function of cell associated plasminogen activators which have been proposed to facilitate keratinocyte migration during wound healing.

Thrombomodulin's correlation with epidermal cell differentiation supports the use of exogenous human thrombomodulin as a treatment in wound healing to prevent scar formation, to accelerate healing of chronic wounds such as chronic leg ulcers in diabetic patients, burns or chemotheraphy-induced wounds, and for treatment of skin diseases caused by thrombin over stimulation (associated with disfunctional regulation of fibroblast or keratinocytes) including psoriasis, hyperkeratosis, lichen planus, scleroderma, morphea, lichen sclerosis et atrophica and to accelerate healing of noncutaneous wounds such as oral ulcers, vaginal ulcers, or osophageal ulcers. According to the present invention, thrombomodulin or derivatives of thrombomodulin are administered either systemically; i.e. intravaneous, subcutaneous, or intramuscular injection or topically; as a component of a cream or ointment. The presence of excess thrombomodulin in the wound will prevent over-stimulation by thrombin and thus facilitate tissue repair.

Preparations for thrombomodulin treatment may include either a full-length recombinant human thrombomodulin protein or derivatives of full-length recombinant human thrombomodulin. Such derivatives could include soluble thrombomodulin (with transmembrane, cytoplasmic and other domains deleted) or glycosylation variants of thrombomodulin (with altered O-linked oligosaccharide chains, N-linked oligosaccharide chains, or glycosaminoglycan chains). Glycosamino glycan-contained derivatives of thrombomodulin would have decreased bioavailability when given systemically but this may not be a problem if thrombomodulin is given topically. Any active derivative of human thrombomodulin will need to retain the EGF-like domains 4–6 in order to bind thrombin and accelerate protein C activation. See S. R. Lentz, Yan Chen, and J. E. Sandler. 1993. Sequences Required for Thrombomodulin Cofactor Activity Within the Fourth Epidermal Growth Factor-like Domain of Human Thrombomodulin. *Journal of Biological Chemistry*, 268:15312–15317, which is incorporated herein by reference.

Topical administration of thrombomodulin would be preferred in that the greatest thrombin inhibition would occur at the superficial surface of a wound which would decrease superficial scarring due to excess thrombin while allowing thrombin in the deep layers to continue to stimulate other aspects of tissue repair. Thrombomodulin would need to be administered in amounts to exceed the binding affinity for thrombin in purified systems.

EXAMPLE 1

Thrombomodulin Correlates with Epidermal Cell Differentiation

Materials. Thrombin and protein C were purified from human plasma as described previously. (Tsiang, M., S. R. Lentz, W. A. Dittman, D. Wen, E. M. Scarpati, and J. E. Sadler. 1990. Equilibrium Binding of Thrombin to Recombinant Human Thrombomodulin: Effect of Hiurdin, Fibrinogen, Factor Va, and Peptide Analogues. *Biochemistry* 29:10602–10612.) Human antithrombin III was a gift of Dr. Douglas Tollefsen (Washington University, St. Louis, Mo.). Restriction enzymes Mlu I and Bgl γT, and T4 polynucleotide kinase were purchased from New England Biolabs (Beverly, Mass.). Nuclease S1 was obtained from United States Biochemical Corporation (Cleveland, Ohio), and calf intestinal alkaline phosphatase was from Boehringer Mannheim Biochemicals (Indianapolis, Ind.). [$\gamma^{32}P$]ATP was purchased from Amersham Corporation (Arlington Heights, Ill.). Triton X-100 was purchased from Fisher Scientific (Pittsburgh, Pa.), S-2366 was obtained from Kabi Pharmacia Hepar, Inc. (Franklin, Ohio), and porcine intestinal heparin was obtained from Elkins-Sinn, Inc. (Cherry Hill, N.J.). Biotinylated horse anti-mouse IgG was purchased from Vector Laboratories (Burlingame, Calif.) and 3,3' diaminobenzidine tetrahydrochloride dihydrate was purchased from Aldrich Chemical Company (Milwaukee, Wis.).

Immunohistochemistry. Immunohistochemical staining was performed with a mouse monoclonal antibody that recognizes an epitope within the fifth epidermal growth factor-like domain of human thrombomodulin. (Tsiang, M., S. R. Lentz, and J. E. Sadler. 1992. Functional Domains of Membrane-Bound Human Thrombomodulin. EGF-Like Domains Fourt to Six and the Serine/Threonine-Rich Domain are Required for Cofactor Activity. *J. Biol. Chem.* 267:6164–6170.) This antibody has been demonstrated to bind specifically to both natural (Maruyama, I. and P. W. Majerus. 1985. The Turnover of Thrombin-Thrombomodulin Complex in Cultured Human Umbilical Vein Endothelial Cells and A549 Lung Cancer Cells. *J. Biol. Chem.* 260:15432–15438.) and recombinant (Tsiang, M., S. R. Lentz, J. E. Sadler. 1992. Functional Domains of Membrane-Bound Human Thrombomodulin. EGF-Like Domains Fourt to Six and the Serine-Threonine-Rich Domain are Required for Cofactor Activity. *J. Biol. Chem.* 267:6164–6170) human thrombomodulin. Formalin-fixed, paraffin embedded sections of normal skin, invasive squamous cell carcinoma, and basal cell carcinoma of the skin were deparaffinized in xylene, rehydrated in graded alcohols to water, and rinsed in PBS. Endogenous peroxidase activity was blocked with 0.3% (v/v) $H_2O_2$ for 30 minutes at room temperature. Non-specific background staining was prevented by application of normal horse serum (Vector Laboratories, Burlingame, Calif.). Sections were then incubated with mouse anti-human thrombomodulin IgG for two hours at room temperature, rinses with PBS, incubated with biotinylated horse anti-mouse IgG for 30 minutes at room temperature, rinsed with PBS, and covered with avidin-biotin-peroxidase complex (Vector Laboratories, Burlingame, Calif.). After 30 minutes at room temperature, the sections were rinses with PBS, and peroxidase staining was demonstrated by incubation with 0.05% (w/v) 3,3' diaminobenzidine tetrahydrochloride dihydrate. A counterstain of 10% Harris hematoxylin was applied prior to coverslipping. Negative control slides were prepared by substituting pre-immune mouse serum for the primary antibody. Staining intensity was scored as (–) negative, (+) weakly positive, (++) moderately positive, or (+++) strongly positive. Identically treated sections or lung and placenta were used as positive controls for thrombomodulin expression.

Cell culture. Human keratinocytes were isolated from neonatal foreskins after overnight incubation in 0.25% trypsin/0.1% sucrose solution at 4° C. Cells were plated at a density of approximately $4\times10^1$ cells/cm$^2$ (one foreskin/60 mm plate) and cultured for three to five passages in serum-free keratinocyte growth medium (KCM)[1] (Clonetics Corporation, San Diego, Calif.) containing 0.07 mM calcium chloride (Knedler, A. and R. G. Ham. 1987. Optimized Medium for Clonal Growth of Human Microvascular Endothelial Cells with Minimal Serum. *In Vitro Cell. Devel. Biol.* 23:481–491). After reaching 80% confluency during the terminal passage, keratinocytes were incubated in KGM containing 1.4 mM calcium chloride to induce squamous differentiation. This "calcium switch" method has been demonstrated to promote keratinocyte differentiation by both morphologic and biochemical criteria (Boyce, S. T. and R. G. Ham. 1983. Calcium-Regulated Differentiation of Normal Human Epidermal Keratinocytes in Chemically Defined Clonal Culture and Serum-Free Serial Culture. *J. Invest. Dermatol.* 81:335–405; Pillai, S., D. D. Bilke, M. Hincenbergs, and P. M. Elias. 1988. Biochemical and Morphological Characterization of Growth and Differentiation of Normal Human Keratinocytes in a Serum-Free Medium. *J. Cell. Physiol.* 134:229–237; Pillai, S., D. D. Bilke, M. Mancianti, P. Cline, and M. Hincenbergs. 1990. Calcium Regulation of Growth and Differentiation of Normal Human Keratinocytes: Modulation of Differentiation Competence by Stages of Growth and Extracellular Calcium. *J. Cell. Physiol.* 143:294–302). Human umbilical vein endothelial cells (HUVEC) were purchased from Clonetics Corporation (San Diego, Calif.) and cultured for three to seven passages in endothelial cell growth medium as described previously (Lentz, S. R. and J. E. Sadler. 1991. Inhibition of Thrombomodulin Surface Expression and Protein C activation by the Thrombogenic Agent Homocysteine. *J. Clin. Invest,* 88:1906–1914).

[1] Abbreviations used: HUVEC, human umbilical vein endothelial cells; KGM, keratinocyte growth medium.

Thrombomodulin cofactor activity. Adherent cultures of keratinocytes or HUVEC were washed with PBS, and cells were collected by scraping. Cell suspensions were centrifuged at 1000×g for 5 minutes, and the pellets were resuspended in 100 µl of 20 mM tris-HCl, pH 8.0, 0.6% (v/v) triton X-100, 100 mM NaCl, 3 mM $CaCl_2$. After incubation for 5 minutes at room temperature, nuclei and cellular debris were removed by centrifugation. Thrombomodulin cofactor activity was measured by a modification of a two stage protein C activation assay described previously (Tsiang, M., S. R. Lentz, W. A. Dittman, D. Wen, L. M. Scarpati, and J. E. Sadler, 1990. Equilibrium Binding of Thrombin to Recombinant Human Thrombomodulin: Effect of Hirudin, Fibrinogen, Factor Va, and Peptide Analogues. *Biochemistry* 29:10602–10612). In the first stage, cell lysates were incubated for 30 minutes at 37° C. in assay buffer (50 mM Tris-HCl, pH 8.0, 0.1M NaCl, 1% bovine serum albumin) containing 2.6 nM human thrombin, 0.84 µM human protein C, and 2.4 mM $CaCl_2$. The reaction was stopped by addition of 25 µg/ml antithrombin III and 25 units/ml heparin. In the second stage, the amidolytic activity of activated protein C was measured by determining the rate of hydrolysis of the chromogenic substrate S-2366 (L-pyroglutamyl-L-prolyl-L-arginine-p-nitroaniline hydrochloride). Cofactor activity, defined as the rate of thrombomodulin-dependent formation of activated protein C, was calculated from a standard curve generated with human activated protein C (Haematologic Technologies Inc., Essex, Vt.). The total protein concentration of cell lysates was determined by a modified Bradford protein assay (Bio-Rad Laboratories, Hercules, Calif.).

Thrombomodulin antigen assay. The concentration of thrombomodulin antigen in cell lysates was measured by a sandwich ELISA that utilizes two mouse monoclonal anti-human thrombomodulin antibodies with non-overlapping epitopes (Diagnostica Stago, France).

Nuclease S1 protection analysis. Plasmids containing cDNA inserts for human thrombomodulin (pUC19TM12 (Lentz, S. R., M. Tsiang, and J. E. Sadler, 1991. Regulation of Thrombomodulin by Tumor Necrosis factor-α: Comparison of Transcriptional and Posttranscriptional Mechanisms. *Blood* 77:542 550)) and human γ actin (pHFγA-1, provided by Dr. L. Kedes, University of Southern California, Pasadena, Calif. (Gunning D., P. Ponte, H. Okayama, J. Engle, H. Blau, and L. Kedes. 1983. Isolation and Characterization of Full-Length cDNA clones for human α,-β-, and gamma-actin mRNAs: Skeletal but not Cytoplasmic Actins Have an Amino-Terminal Cysteine That is Subsequently Removed. *Mol. Cell. Biol.* 3:787–795)) were linearized by digestion with Mlu I and Bgl II, respectively. The linearized plasmids were treated with calf intestinal alkaline phosphatase and end-labeled with $[\gamma^{32}P]ATP$ and T4 polynucleotide kinase. Total cellular RNA was isolated from cultured cells by acid guanidinium thiocyanate-phenol-chloroform extraction (Chomoczynski, P. and N. Sacchi. 1987. Single-Step Method of RNA Isolation by Acid Guanidinium Thiocyanate-Phenol-Chloroform Extraction. *Anal. Biochem.* 162:156–159). The end-labeled thrombomodulin and actin plasmids were hybridized overnight at 55° C. with 50 µg or 5 µg of total cellular RNA, respectively. Hybridization conditions, nuclease S1 digestion, and analysis on denaturing PAGE were performed as described previously (Lentz, S. R., M. Tsiang, and J. E. Sadler. 1991. Regulation of Thrombomodulin by Tumor Necrosis Factor-α:Comparison of Transcriptional and Posttranscriptional Mechanisms. *Blood* 77:542–550). Gels were analyzed by autoradiography, and the thrombomodulin and actin fragments were quantitated by direct radioanalytic imaging (Ambis Radioanalytic Systems, San Diego, Calif.).

Figure 1B:
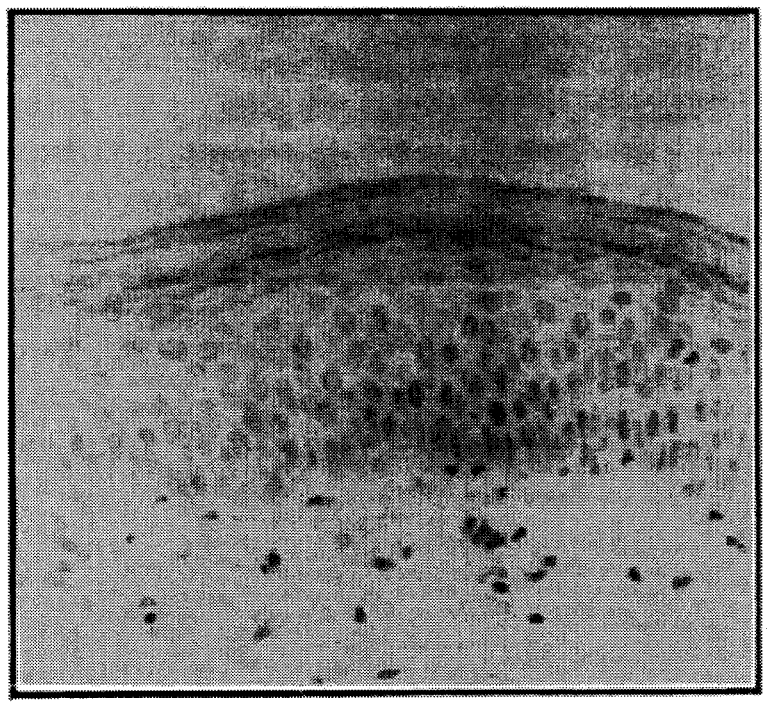

Thrombomodulin expression in normal human epidermis. To examine the expression of thrombomodulin in epidermis, immunohistochemical staining was performed on 13 biopsy specimens containing normal human skin. In all specimens examined, specific thrombomodulin staining was observed in a consistent pattern: no staining was detected in the basal layer of keratinocytes, but strong staining was observed in several suprabasal layers of spinous keratinocytes. Thrombomodulin staining decreased in intensity progressively in the granular layer of keratinocytes, and was not detected in the cornified layer (FIG. 1A). Staining was concentrated at the periphery of cells, suggesting that keratinocyte thrombomodulin is expressed primarily on the cell surface. As expected, endothelial cells of dermal capillaries also stained for thrombomodulin, although the intensity of staining was generally less than that of keratinocytes. No staining was observed when pre-immune mouse serum was substituted for the anti-thrombomodulin antibody (FIG. 1B). These results confirm that thrombomodulin is present in human epidermis, and suggest that thrombomodulin is selectively expressed early in keratinocyte differentiation.

Thrombomodulin expression in epidermal malignancies. To determine if thrombomodulin is also expressed by malignant human keratinocytes, immunohistochemical staining was performed on five cases each of invasive squamous cell carcinoma and basal cell carcinoma of the skin. Based on the degree of keratinization, three cases of squamous cell carcinoma were classified as well-differentiated, one as moderately-differentiated, and one as poorly-differentiated (Table I).

TABLE I

IMMUNOHISTOCHEMICAL STAINING OF THROMBOMODULIN INSQUAMOUS CELL CARCINOMAS (SCC) AND BASAL CELL CARCINOMAS (BCC) OF THE SKIN

| Case | Diagnosis | Site | Keratinization (%) | Thrombomodulin Staining |
|---|---|---|---|---|
| 1 | SCC | chest | 90 | +++ |
| 2 | SCC | temple | 5 | ++ |
| 3 | SCC | submental | 80 | +++ |
| 4 | SCC | ear | 30 | +++ |
| 5 | SCC | neck | 90 | +++ |
| 6 | BCC | ear | 0 | − |
| 7 | BCC | face | 0 | − |
| 8 | BCC | proauricular | 5 | −+ |
| 9 | BCC | chin | 0 | − |
| 10 | BCC | nose | 0 | − |

*Weak (+) thrombomodulin staining was seen in areas of focal squamous differentiation.

Figure 1C:
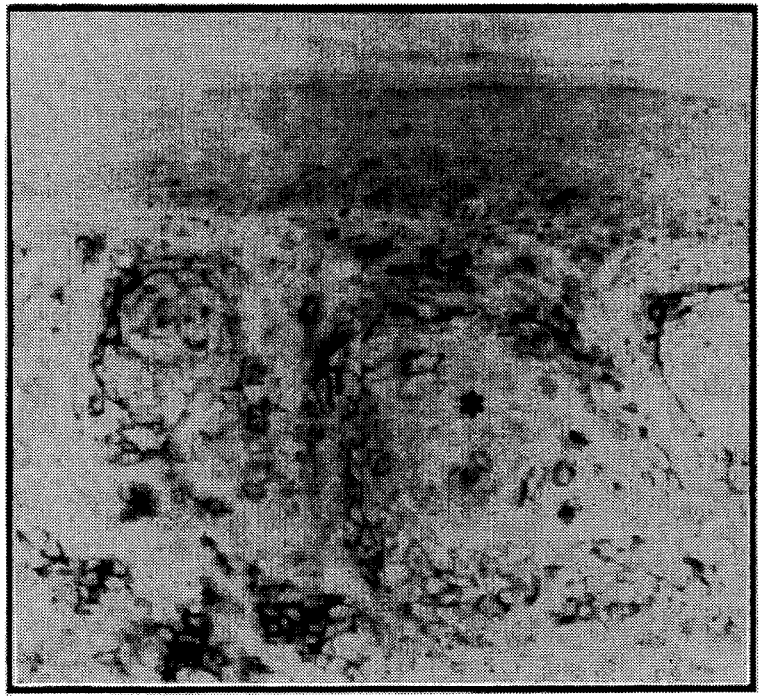
Figure 1D:
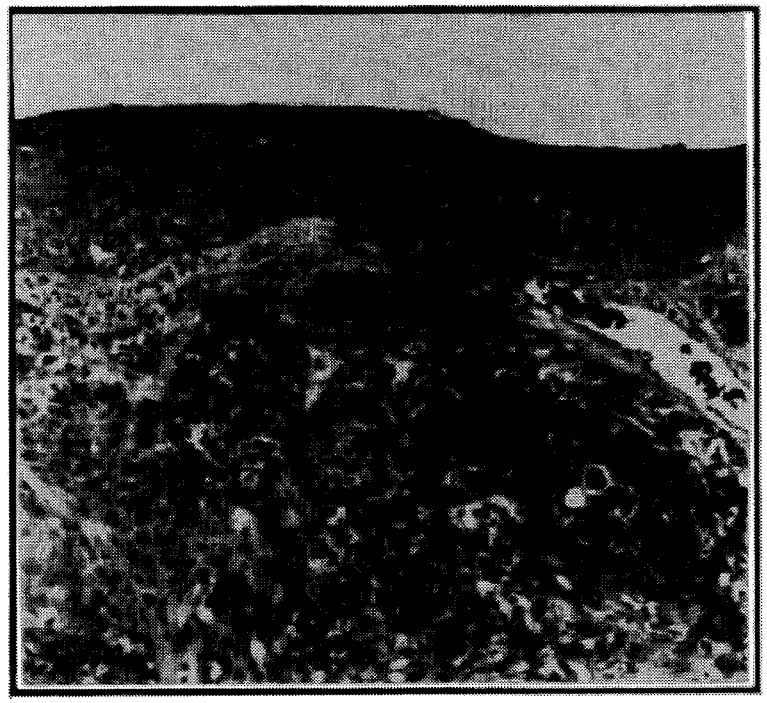
Figure 1E:
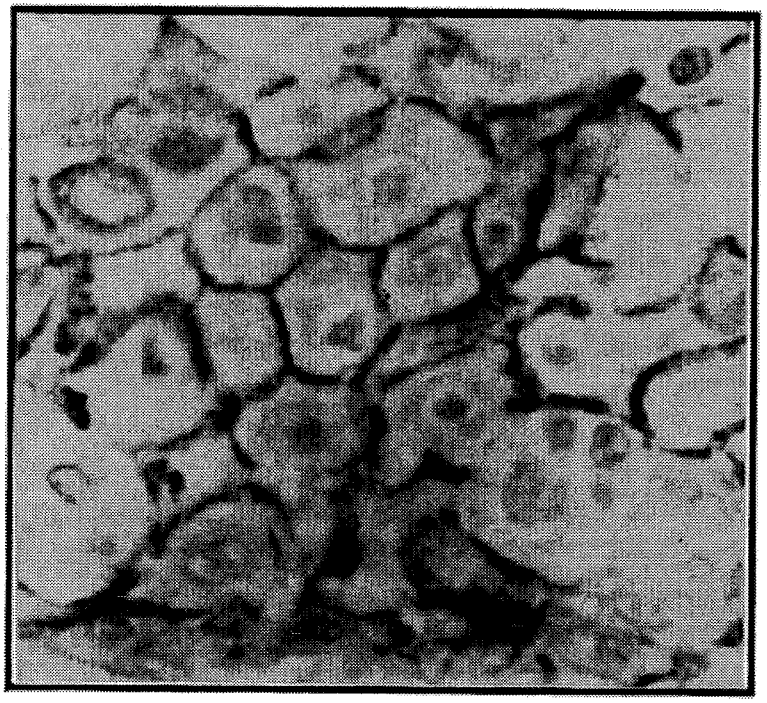
Figure 1F:
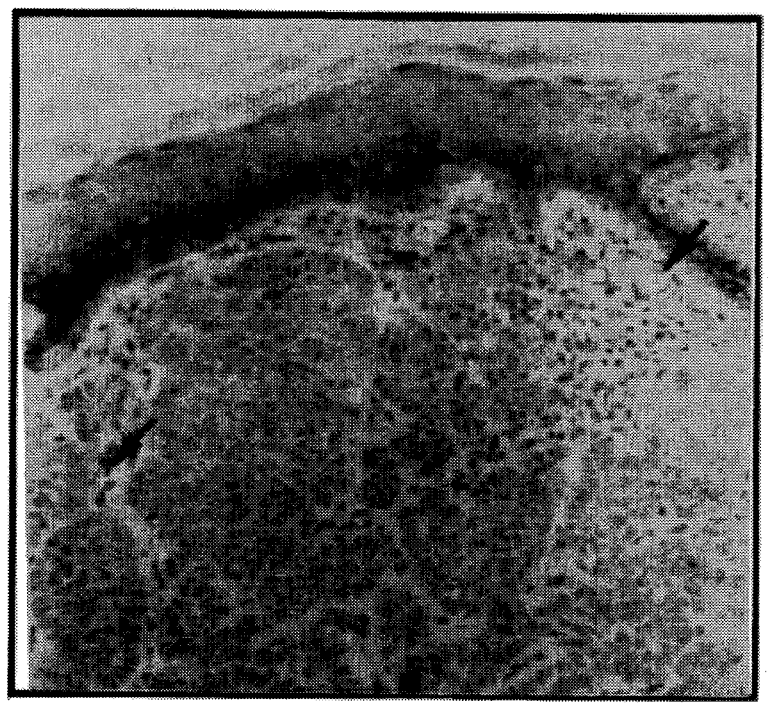

In all cases of squamous cell carcinoma, specific thrombomodulin staining was observed in both the neoplastic cells and in the adjacent normal epidermis. Within invasive nests of tumor cells, non-keratinized peripheral cells stained strongly while central, more highly keratinized cells stained weakly or were negative (FIGS. 1C and 1D). Interestingly, a diffuse cytoplasmic pattern of staining was seen in the poorly-differentiated squamous cell carcinoma, while the more differentiated neoplasma stained primarily in a membrane-specific pattern similar to that of normal epidermis (FIG. 1E). In four of five cases of basal cell carcinoma, no thrombomodulin staining of neoplastic cells was seen, although specific thrombomodulin staining of vascular endothelial cells was observed (FIG. 1F). On one case of basal cell carcinoma, weak thrombomodulin staining of tumor cells was seen in areas of focal squamous differentiation (Table I). These results demonstrate that thrombomodulin expression correlates with squamous differentiation in both normal and neoplastic keratinocytes.

Thrombomodulin expression in cultured keratinocytes. To determine if the relationship between thrombomodulin expression and epidermal differentiation observed in vivo is reproduced in vitro, we measured the synthesis and activity of thrombomodulin in primary cultures of human foreskin keratinocytes. Our initial studies were performed with keratinocytes cultured in serum-free medium containing 0.07 mM calcium chloride, a condition that inhibits squamous differentiation (Boyce, S. T. and R. G. Ham. 1983. Calcium-Regulated Differentiation of Normal Human Epidermal Keratinocytes in Chemically Defined Clonal Culture and Serum-Free Serial Culture. *J. Invest. Dermatol.* 81:335–405; Pillai, S., D. D. Bilko, M. Hincenbergs, and P. M. Elias. 1988. Biochemical and Morphological Characterization of Growth and Differentiation of Normal Human Keratinocytes in a Serum-Free Medium. *J. Cell. Physiol.* 134:229–237; Pillai, S., D. D. Bilke, M. Mancianti, P. Cline, and M. Hincenbergs. 1990. Calcium Regulation of Growth and Differentiation of Normal Human Keratinocytes: Modulation of Differentiation Competence by States of Growth and Extracellular Calcium. *J. Cell. Physiol.* 143:294–302). The concentration of thrombomodulin antigen in keratinocyte lysates was determined by ELISA, and thrombomodulin cofactor activity was measured in a two-stage protein C activation assay. Compared to HUVEC lysates, keratinocyte lysates contained approximately 50% lower amounts of both thrombomodulin antigen and cofactor activity (Table II).

TABLE II

THROMBOMODULIN ANTIGEN AND COFACTOR ACTIVITY IN CELL LYSATES

| Lysate | Antigen ug/mg * | Cofactor Acitivity pmol/h/mg ** | Specific Activity mol/h/mol *** |
|---|---|---|---|
| Keratinocytes | 0.17 ± 0.04 | 48 ± 13 | 21 ± 4 |
| HUVEC | 0.42 ± 0.11 | 95 ± 16 | 18 ± 6 |

*Thrombomodulin antigen was measured by ELISA, and is expressed as µg of thrombomodulin per mg of total cellular protein.
**Thrombomodulin cofactor activity was measured in a protein C activation assay, and is expressed as pmol of activated protein C per hour per mg of total cellular protein.
***Specific activity is expressed as mole of activated protein C per hour per mole of thrombomodulin. Values represent the mean ±SD of five determinations for keratinocytes, and six determinations for HUVEC.

The specific activities of keratinocyte and HUVEC lysates were similar, however, indicating that thrombomodulin synthesized by proliferating human keratinocytes is comparable to endothelial cell thrombomodulin in its ability to promote protein C activation by thrombin.

Figure 2A:
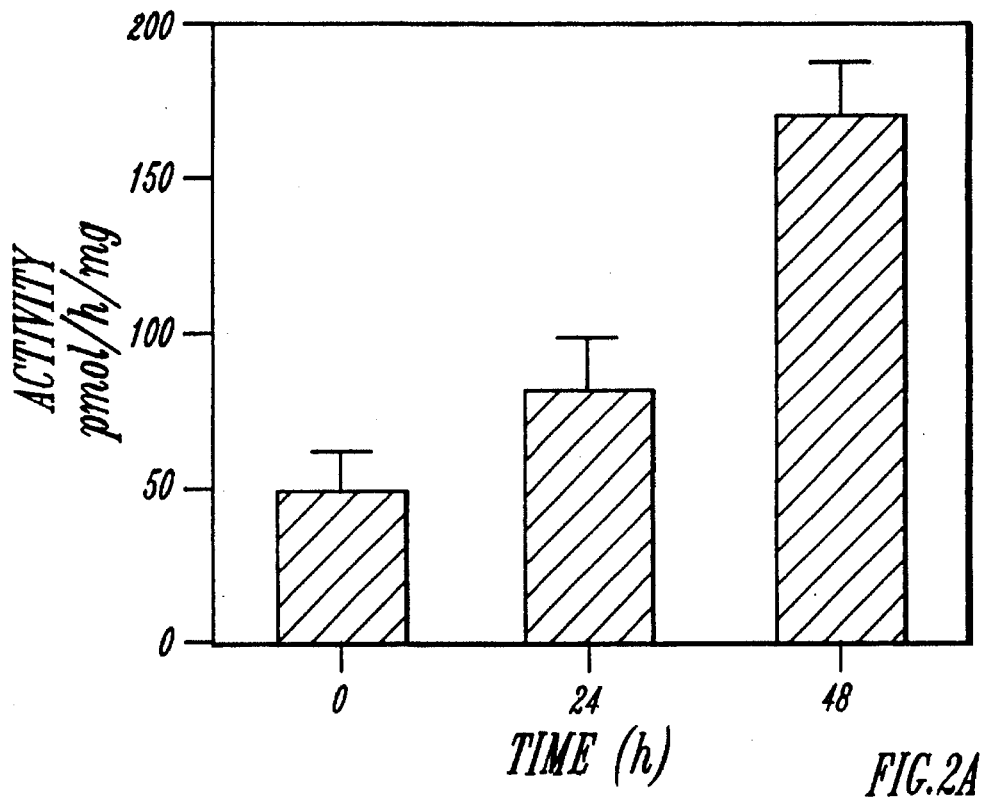
FIGS. 2A–2B show the induction of thrombomodulin activity and antigen in cultured human keratinocytes. Keratinocytes were incubated for the indicated times in KGM containing 1.4 mM calcium chloride, and coil lysates were assayed for thrombomodulin cofactor activity (A) and thrombomodulin antigen (B). Values represent the mean ±SD of five determinations.
Figure 2B:
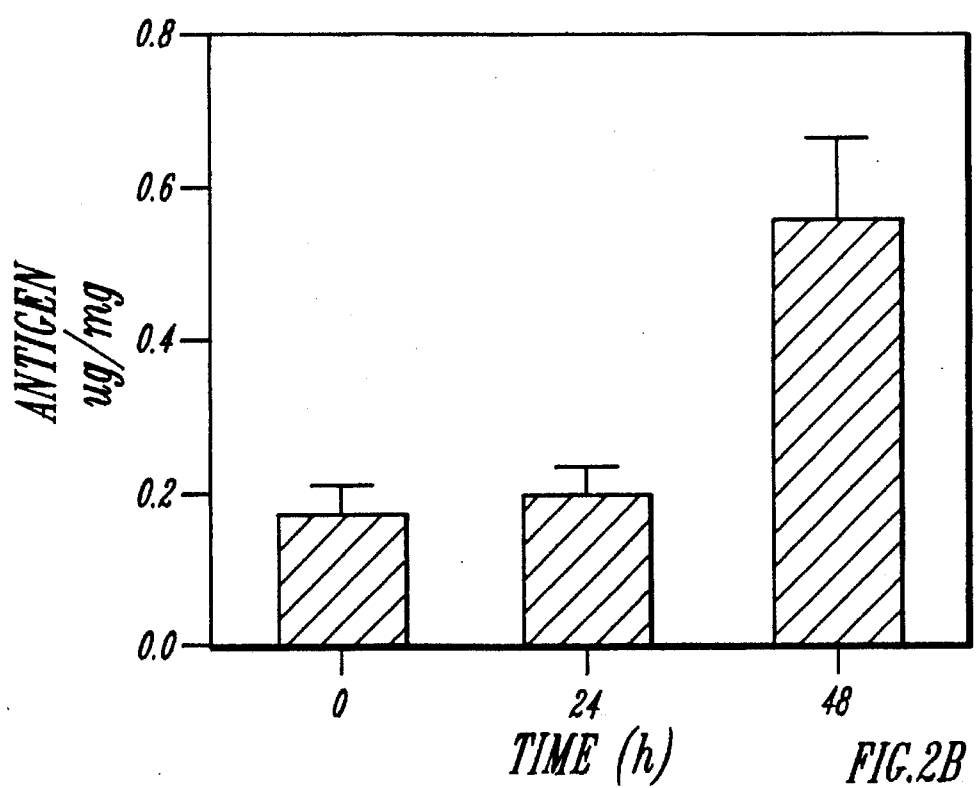

Next measured thrombomodulin activity in differentiating keratinocytes. After keratinocytes were cultured to 80% confluency in the presence of 0.07 mM calcium chloride, the calcium chloride concentration of the medium was increased to 1.4 mM. This concentration of calcium has been shown to induce both structural and biochemical features of terminal differentiation in cultured keratinocytes (Boyce, S. T. and R. G. Ham. 1983. Calcium-Regulated Differentiation of Normal Human Epidermal Keratinocytes in Chemically Defined Clonal Culture and Serum-Free Serial Culture. *J. Invest. Dermatol.* 81:335–405; Pillai, S., D. D. Bilke, M. Hincenbergs, and P. M. Elias. 1988. Biochemical and Morphological Characterization of Growth and Differentiation of Normal Human Keratinocytes in a Serum-Free Medium, J. Cell. Physiol. 134:229–237; Pillai, S., D. D. Bilke, M. Mancianti, P. Cline, and M. Hincenbergs. 1990. Calcium Regulation of Growth and Differentiation of Normal Human Keratinocytes: Modulation of Differentiation Competence by Stages of Growth and Extracellular Calcium. *J. Cell. Physiol.* 143:294–302). In the presence of 1.4 mM calcium chloride, the thrombomodulin cofactor activity of keratinocyte lysates increased by 1.7-fold after 24 hours, and by 3.5-fold after 48 hours (FIG. 2A). The 3.5-fold increase in thrombomodulin cofactor activity after 48 hours was associated with a 3.2-fold increase in thrombomodulin antigen (FIG. 2B), indicating that the specific activity of thrombomodulin did not change appreciably during differentiation. These results demonstrate that the correlation between thrombomodulin expression and squamous differentiation seen by immunohistochemistry in vivo is partially reproduced in calcium-treated keratinocytes.

Figure 3:
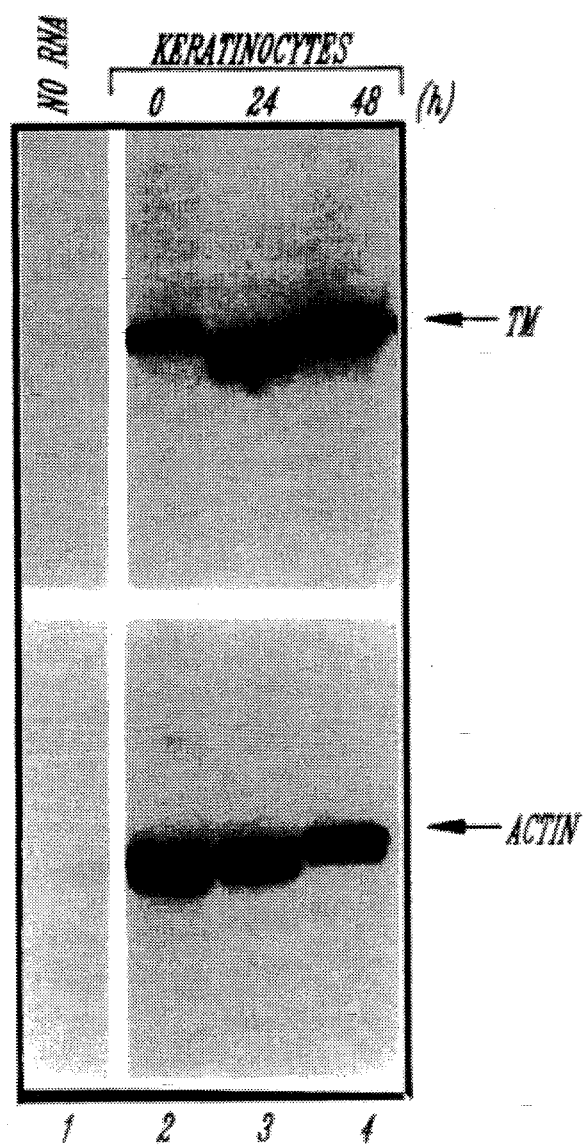
FIG. 3 depicts induction of thrombomodulin mRNA in cultured keratinocytes. Nuclease S1 protection analysis of thrombomodulin (TM) and actin mRNA was performed with total cellular RNA isolated from Keratinocytes incubated in KGM containing 1.4 mM calcium chloride for 0 (lane 2), 24 (lane 3), or 48 (lane 4) hours. In lane 1, digestion with nuclease S1 was performed in the absence of RNA.

To determine if the increase in cofactor activity observed during keratinocyte differentiation is associated with an increase in thrombomodulin mRNA, nuclease S1 protection assays were performed. Total cellular RNA was hybridized to radiolabeled human thrombomodulin and actin probes, digested with nuclease S1, and subjected to denaturing PAGE and autoradiography (FIG. 3). Thrombomodulin mRNA was readily detected in keratinocytes cultured in the presence of 0.07 mM calcium chloride (lane 2), and increased progressively after incubation for 24 and 48 hours in medium containing 1.4 mM calcium chloride (lanes 3 and 4). These incubation conditions did not affect the quantity of actin mRNA. No protected fragments were seen when hybridizations were performed in the absence of RNA (lane 1). Quantiation by direct radioanalytic imaging revealed that thrombomodulin mRNA, normalized to actin mRNA, increased by 4.5-fold after keratinocytes were incubated with 1.4 mM calcium chloride for 48 hours. This suggests that the increase in thrombomodulin in differentiating keratinocytes is mediated by an increase in thrombomodulin mRNA.

EXAMPLE 2 (Prophetic)

Therapeutic Application of Thrombomodulin to Stimulate Wound Regeneration and Prevent Scarring Because thrombomodulin is currently acceptable as a therapeutic anticoagulant in humans, much preliminary testing has already been performed, and supports its use in humans as a therapeutic agent. Thrombomodulin or its derivatives would be administered topically in concentrations calculated to exceed the known binding affinity for thrombin in purified systems. The equilibrium binding constant for thrombin-thrombomodulin interaction varies from approximately 0.5 to 5 nM in most purified systems. Thus concentration of thrombomodulin would be at concentrations of 1.0 nM and increasing to 100 nM.

Amounts administered would be that which is sufficient to bind thrombin present at the wound site and will likely be in a range of 75 ng/ml to 7.5 µg/ml. Additionally a pharmaceutically acceptable carrier such as saline may be employed. This corresponds to a total dose of 0.375 to 37.5 µg in a 5 milliliter topical application.

What is claimed is:

1. A method of stimulating wound regeneration and decreasing scar formation in animals comprising:
   administering to said animal an effective amount of thrombomodulin.

2. The method of claim 1 wherein said wound is a cutaneous wound.

3. The method of claim 1 wherein said wound is a non-cutaneous wound.

4. The method of claim 3 wherein said noncutaneous wound is selected from the group consisting of: oral ulcers, vaginal ulcers and esophageal ulcers.

5. The method of claim 1 wherein said thrombomodulin retains the EGF-like domains four through six.

6. The method of claim 1 wherein said thrombomodulin is soluble thrombomodulin.

7. The method of claim 1 wherein said thrombomodulin is a glycosylation variant with altered chains selected from the group consisting of: an O-linked oligosaccharide chain, an N-linked oligosaccharide chain, and a glycosaminoglycan chain.

8. The method of claim 1 wherein said administration of thrombomodulin is topical, at the wound site.

9. The method of claim 1 wherein said administration is systemically.

10. The method of claim 1 wherein said thrombomodulin is administered in a concentration of from about 1.0 µM to 100 µM.

11. The method of claim 1 wherein said thrombomodulin is administered in an amount of approximately 0.375 to 37.5 µg.

12. A method of treating skin diseases caused by thrombin overstimulation in animals comprising:
    treating said animal with an effective amount of thrombomodulin.

13. The method of claim 12 wherein said disease is selected from the group consisting of: psoriasis, hyperkeratosis, lichen planus, scleroderma, morphea, and lichen sclerosis et atrophica.

14. The method of claim 12 wherein said thrombomodulin retains the EGF-like domains four through six.

15. The method of claim 12 wherein said thrombomodulin is soluble thrombomodulin.

16. The method of claim 12 wherein said thrombomodulin is a glycosylation variant with altered chains selected from the group consisting of: an O-linked oligosaccharide chain, an N-linked oligosaccharide chain, and a glycosaminoglycan chain.

17. The method of claim 12 wherein said thrombomodulin is administered at a concentration of from about 1.0 µM to 100 µM.

18. The method of claim 12 wherein said thrombomodulin is administered in an amount of approximately 0.375 to 37.5 µg.

* * * * *